(12) United States Patent
Liu et al.

(10) Patent No.: US 11,832,924 B2
(45) Date of Patent: Dec. 5, 2023

(54) FLUORESCENCE IMAGING PROCESSING AND COMPUTATION FOR SURGERY

(71) Applicant: The Regents of the University of California, Oakland, CA (US)

(72) Inventors: Shanglei Liu, La Jolla, CA (US); Santiago Horgan, La Jolla, CA (US); David Owens, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 773 days.

(21) Appl. No.: 16/482,190

(22) PCT Filed: Feb. 1, 2018

(86) PCT No.: PCT/US2018/016526
§ 371 (c)(1),
(2) Date: Jul. 30, 2019

(87) PCT Pub. No.: WO2018/144785
PCT Pub. Date: Aug. 9, 2018

(65) Prior Publication Data
US 2020/0187797 A1 Jun. 18, 2020

Related U.S. Application Data

(60) Provisional application No. 62/453,980, filed on Feb. 2, 2017.

(51) Int. Cl.
*A61B 5/0275* (2006.01)
*A61B 5/00* (2006.01)
(Continued)

(52) U.S. Cl.
CPC .......... *A61B 5/0275* (2013.01); *A61B 5/0071* (2013.01); *A61B 5/0084* (2013.01);
(Continued)

(58) Field of Classification Search
CPC ... A61B 5/0275; A61B 5/0071; A61B 5/0084; A61B 5/725; A61B 5/742; A61B 5/0295;
(Continued)

(56) References Cited

U.S. PATENT DOCUMENTS

2002/0183621 A1 12/2002 Pfeiffer et al.
2005/0182434 A1 8/2005 Docherty et al.
(Continued)

FOREIGN PATENT DOCUMENTS

WO WO-2004/052195 A1 6/2004

OTHER PUBLICATIONS

International Search Report and Written Opinion dated Apr. 24, 2018, from application No. PCT/US2018/016526.

*Primary Examiner* — David J. McCrosky
*Assistant Examiner* — Nidhi N Patel
(74) *Attorney, Agent, or Firm* — Foley & Lardner LLP

(57) ABSTRACT

Methods for dynamically evaluating blood flow are provided. The method may include injecting Indocyanine Green (ICG) into the bloodstream of a patient, such that the ICG perfuses into a tissue of the patient. ICG images of the tissue may be recorded and stored, such that a user may select a range of stored ICG images. Data indicative of the selected range of stored ICG images is automatically normalized and background-filtering, and a dynamic representation of the ICG perfusion may be generated as a function of time based on the normalized and filtered data. As such, a clinical decision may be made based on the dynamic representation of the ICG perfusion.

6 Claims, 9 Drawing Sheets

Figure 1:
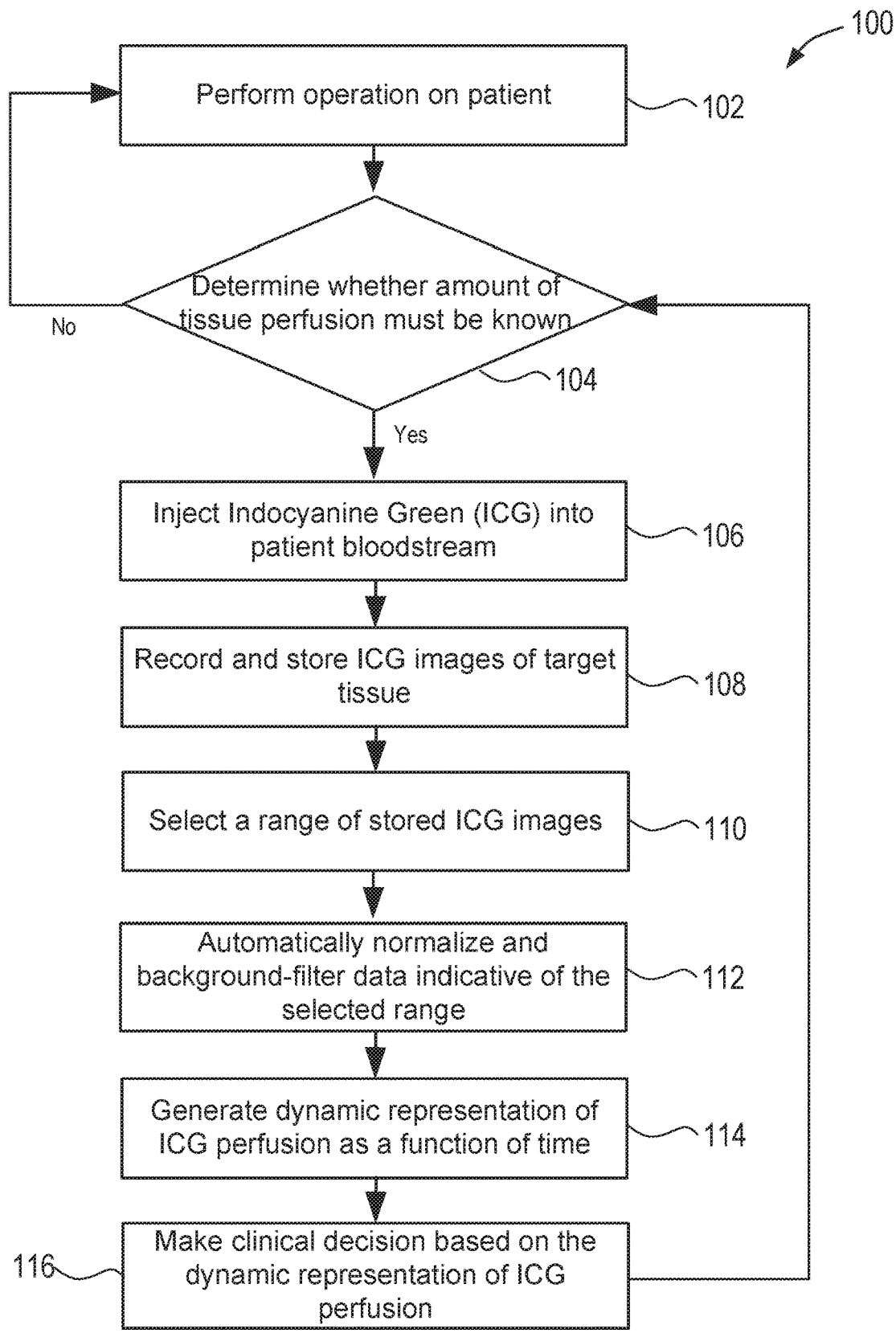

(51) Int. Cl.
   *A61B 1/00* (2006.01)
   *A61B 1/04* (2006.01)
   *A61K 49/00* (2006.01)

(52) U.S. Cl.
   CPC .............. *A61B 5/725* (2013.01); *A61B 5/742* (2013.01); *A61B 1/00096* (2013.01); *A61B 1/043* (2013.01); *A61K 49/0034* (2013.01)

(58) Field of Classification Search
   CPC . A61B 5/0261; A61B 5/1464; A61B 5/02007; A61B 5/4836; A61B 1/00096; A61B 1/043; A61K 49/0034
   See application file for complete search history.

(56) References Cited

U.S. PATENT DOCUMENTS

| | | | |
|---|---|---|---|
| 2015/0182137 A1* | 7/2015 | Flower | A61B 5/0295 |
| | | | 600/431 |
| 2016/0278678 A1* | 9/2016 | Valdes | A61B 5/1459 |
| 2017/0079530 A1* | 3/2017 | DiMaio | A61B 5/0261 |
| 2017/0209053 A1* | 7/2017 | Pantelopoulos | A61B 5/02125 |

\* cited by examiner

FLUORESCENCE IMAGING PROCESSING AND COMPUTATION FOR SURGERY

PRIORITY

The present application is a national stage application under 35 U.S.C. § 371 of International Application No. PCT/US2018/016526, filed on Feb. 1, 2018, which claims priority to U.S. provisional application No. 62/453,980 filed Feb. 2, 2017, each of which are incorporated herein by reference in their entirety.

FIELD OF USE

The present disclosure relates generally to medical diagnostic methods and instrumentation and more particularly, to methods and instrumentation for dynamically evaluating blood flow using imaging, such as fluorescent imaging.

Background

Indocyanine Green (ICG) is a chemical that can be used to identify blood flow through fluorescence detection. ICG fluorescence imaging has gained popularity in recent years to evaluate intraoperative tissue perfusion. Currently, ICG fluorescence imaging provides a visual representation of tissue perfusion as a global view. However, this analysis is almost always qualitatively due to lack of reliable standardized measurements of signal intensity. As a result, surgeons are often unable to decipher the clinical significance of intra-operative fluorescent images.

Although some efforts have been put into density analysis, no device or software currently performs dynamic evaluation of blood flow for a surgeon. Current devices only look at the absolute value of intensity of the ICG signals, which is affected by both camera distance and ambient light distractions. Without objective dynamic measurements, practitioners are only limited to snap shot view of the static environment. This snap shot view in time of how much dye is present in a given tissue is not useful in predicting how much blood will flow in and out of tissue as a function of time. This is a problem because it is the dynamics of blood flow that determines tissue perfusion, not how much blood present at a stationary point in time. And because there are no numerical evaluations known in the art of ICG fluorescence imaging that can capture this dynamic aspect of blood flow, practitioners are forced to use the naked eye to make a clinical decision that is not only subjective, but is difficult to assess between cases.

In view of the foregoing drawbacks of previously known apparatus and methods, there exists a need for producing quantitative temporal measurements of tissue perfusion.

SUMMARY

The present disclosure overcomes the drawbacks of previously-known systems by providing methods for dynamically evaluating blood flow.

The method may include injecting Indocyanine Green (ICG) into the bloodstream of a patient, such that the ICG perfuses into a tissue of the patient. The method also may include recording and storing ICG images of the tissue. In addition, the method may include selecting a range of stored ICG images, and automatically normalizing and background-filtering data indicative of the selected range of stored ICG images. In one embodiment, selecting the range of stored ICG images includes collecting pixel data regarding the green channel intensity of the stored ICG images.

In one embodiment, the method includes splitting the recorded ICG images of the tissue into "n" number of frames, and storing the "n" number of frames of the recorded ICG images such that the range of stored ICG images is selected from the "n" number of frames. In addition, normalizing the data may include generating values quantifying blood flow in or around the tissue, and background filtering the data may include accounting for previous ICG injections into the bloodstream of the patient.

The method also may include generating a dynamic representation of the ICG perfusion as a function of time based on the normalized and filtered data. For example, the dynamic representation of the ICG perfusion as a function of time may be indicative of real-time tissue perfusion. The method further may include making a clinical decision based on the dynamic representation of the ICG perfusion as a function of time.

One embodiment may be a method for dynamically evaluating a blood flow, the method comprising: recording images of a tissue of a patient, wherein the images comprise a signal from an imaging agent with which the patient has been injected; storing the recorded images in a memory of a computer system; displaying the stored images to a user of the computer system;
receiving a feedback from the user regarding a selected area in the displayed images;
executing in a processor of the computer system calculations normalizing and/or filtering the signal from the imaging agent for the selected area of the images; and displaying the normalized and/or filtered signal as a function of time to evaluate a blood flow in the tissue of the patient.

Another embodiment may be a system comprising: (a) a camera configured to record images of a tissue of a patient being injected with an imaging agent, said images comprise a signal from the imaging agent; (b) a memory, which is coupled to the camera and which is configured to store the images recorded by the camera; (c) a display configured to display the stored images to a user; (d) a user interface configured to receive a feedback from the user regarding a selected area in the images; and (d) a processing device, which is operatively coupled to the memory, the interface and the display, the processing device is configured to execute calculations normalizing and/or filtering the signal from the imaging agent for the selected area of the images.

Yet another embodiment may be a non-transitory computer readable storage medium comprising instructions that, when executed by a processor, cause the processor to perform operations comprising: receiving a feedback from a user regarding a selected area in images of a tissue of a patient being injected with an imaging agent, said images comprise signal from the imaging agent; and executing calculations normalizing and/or filtering the signal from the imaging agent for the selected area of the images.

FIGURES

FIG. 1 is a flow chart illustrating an exemplary method for dynamically evaluating blood flow in accordance with the principles of the present disclosure.

Figure 2B:
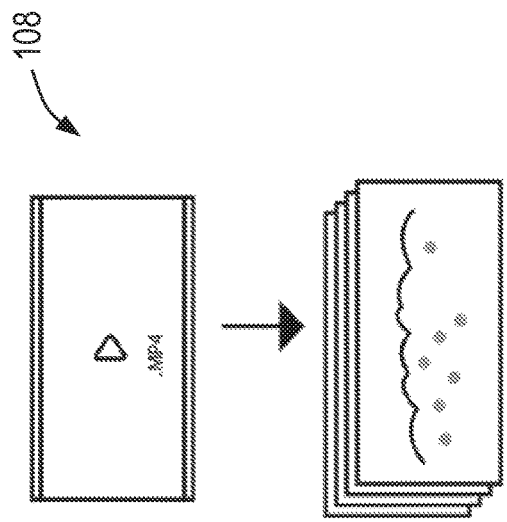
Figure 2D:
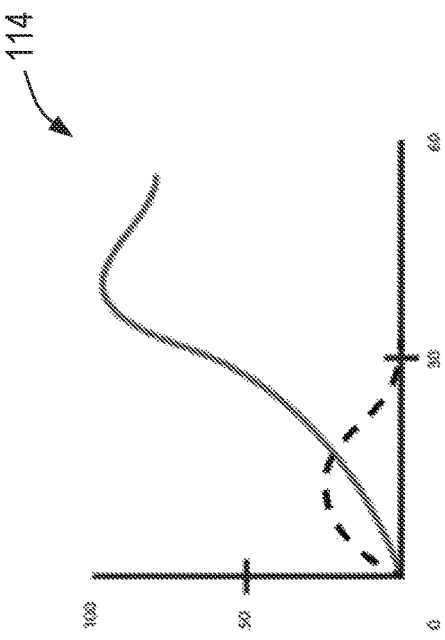
Figure 2A:
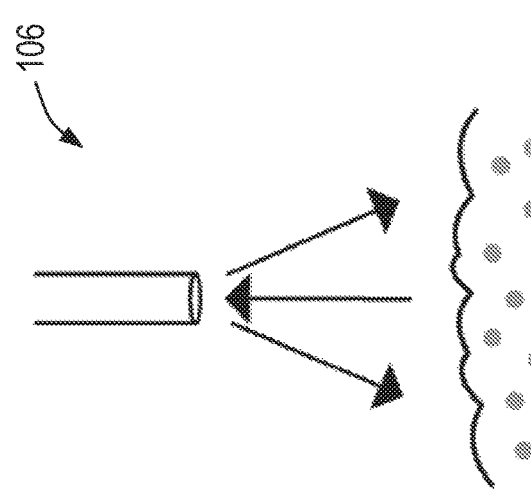
Figure 2C:
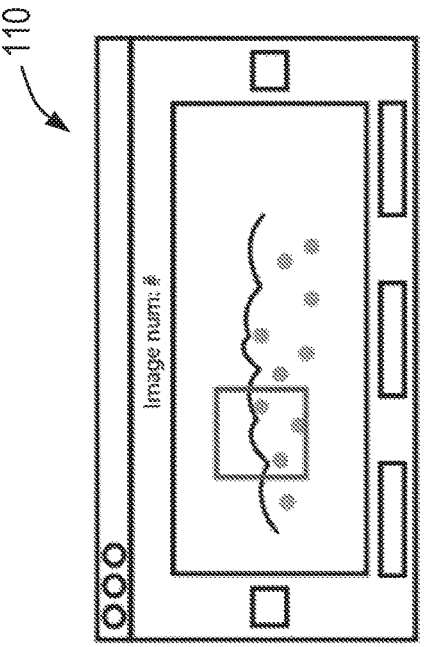

FIGS. 2A-2D illustrate various steps of the exemplary method of FIG. 1. FIG. 2A shows ICG injected into a blood stream of a patient and travel throughout the body where ICG molecules perfuse into tissue. ICG images are collected via existing ICG endoscopic technology. FIG. 2B shows a video from endoscope coppen into "n" number of frames and saved into a directory for an analysis. FIG. 2C shows images loaded into the software where the user can progress forward through the video, image by image and manually select the region of the images where to collect pixel data regarding the green channel intensity of the image. The user can then save this data when they have gone through all the images to a file, such as a .CSV file which may automatically trigger normalization and filtering calculations. FIG. 2D. The data from the saved file, such as the .CSV file, may be then ran through MatLab scripts which do basic calculus to find local/global max's and min's to pinpoint time of interest. This dynamic graph may allow surgeons to determine real time perfusion of tissue.

Figure 3:
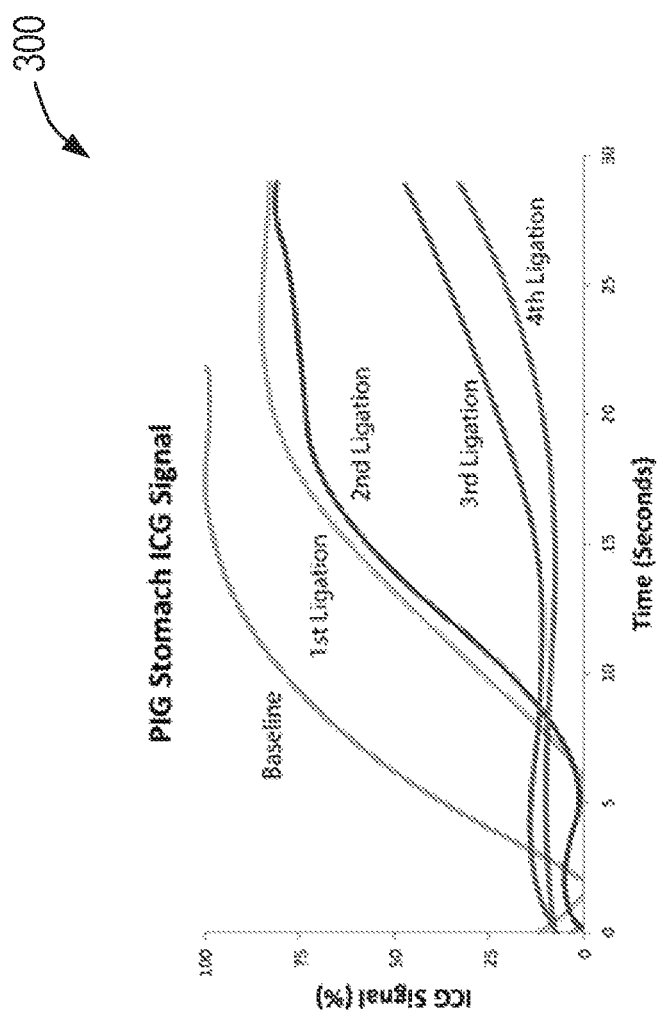

FIG. 3 is a graph illustrating experimental results in accordance with the principles of the present disclosure.

Figure 4:
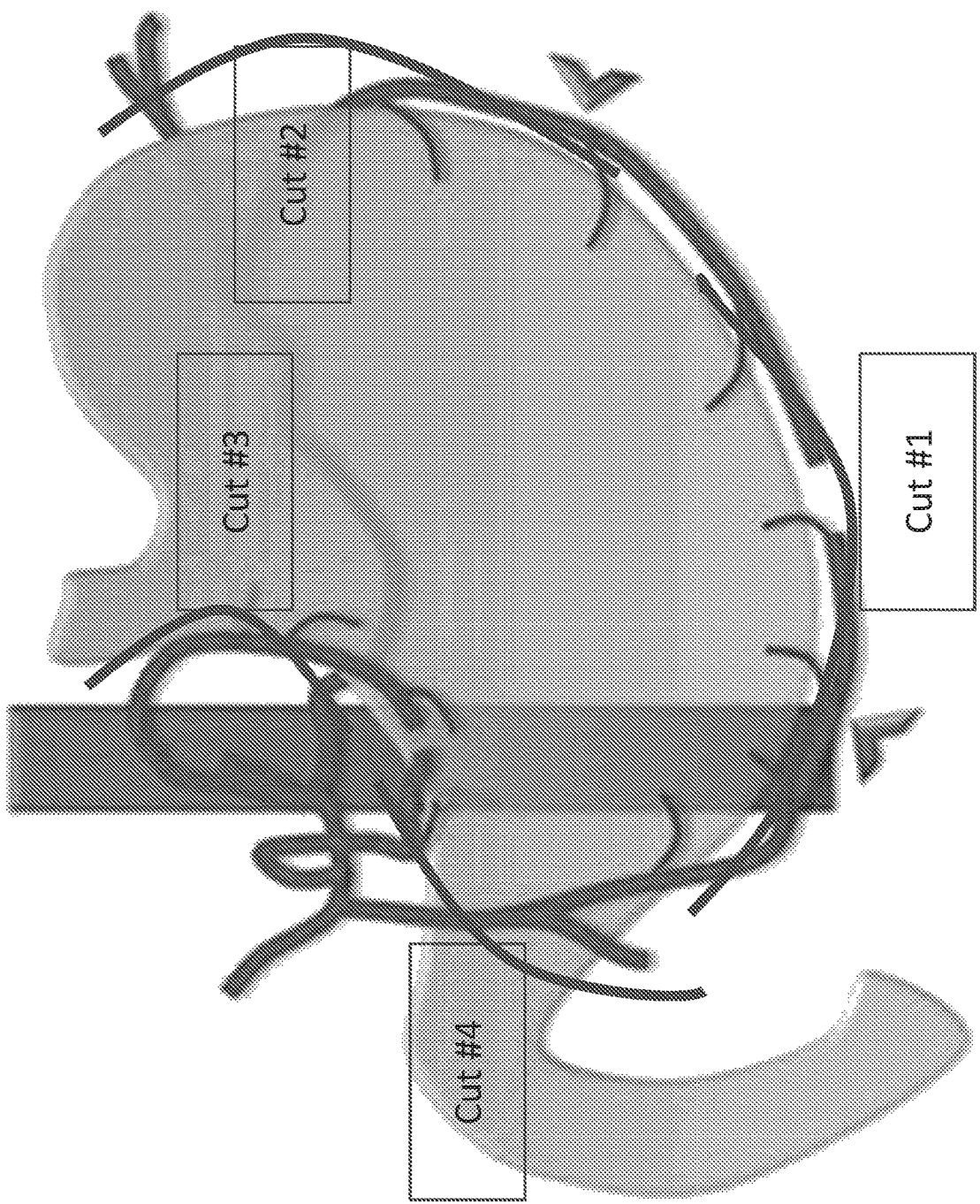

FIG. 4 schematically illustrates cut locations for a pig model. It is difficult to tell from the images how the signal has changed with each blood vessel division by just looking.

Figure 5:
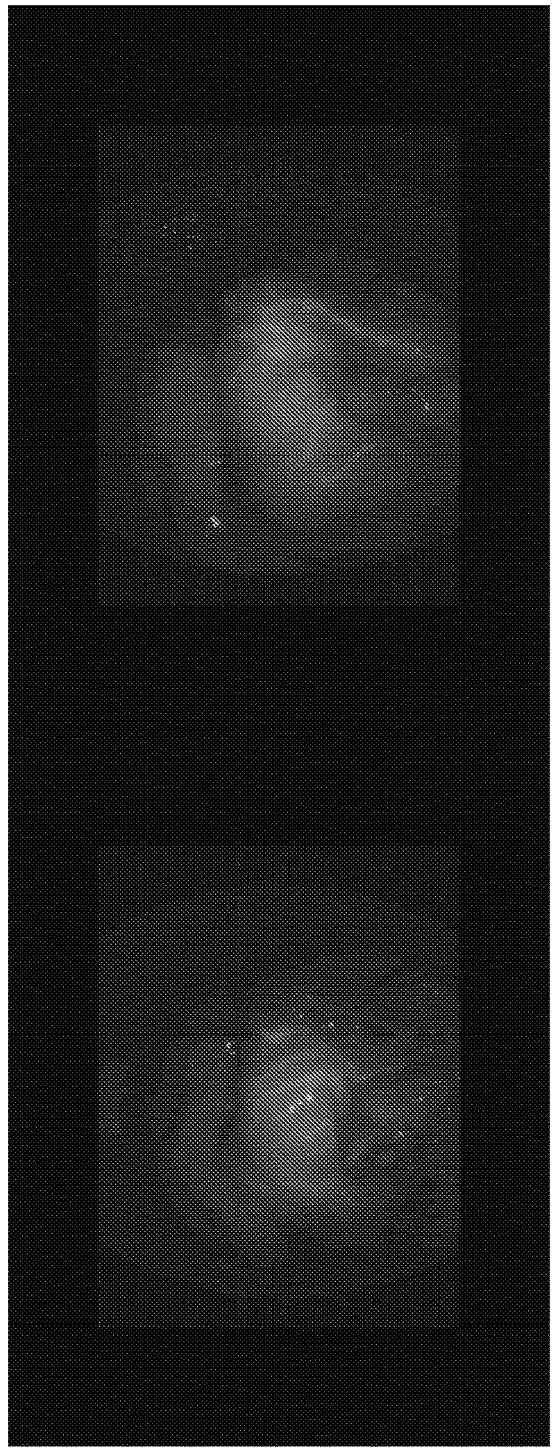
Figure 5:
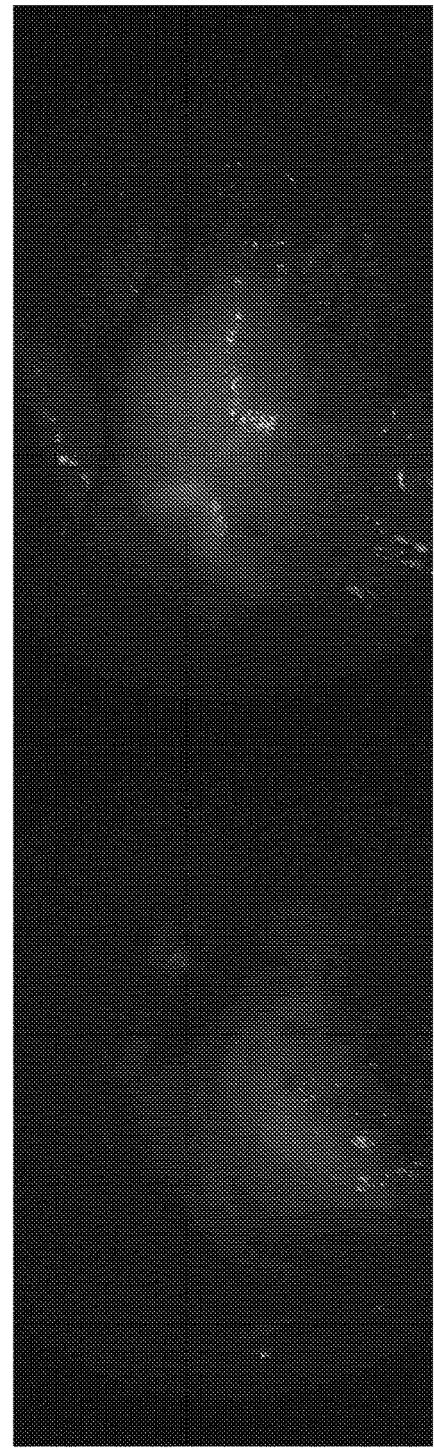

FIG. 5 presents ICG fluorescent images for cuts 1-4.

Figure 6:
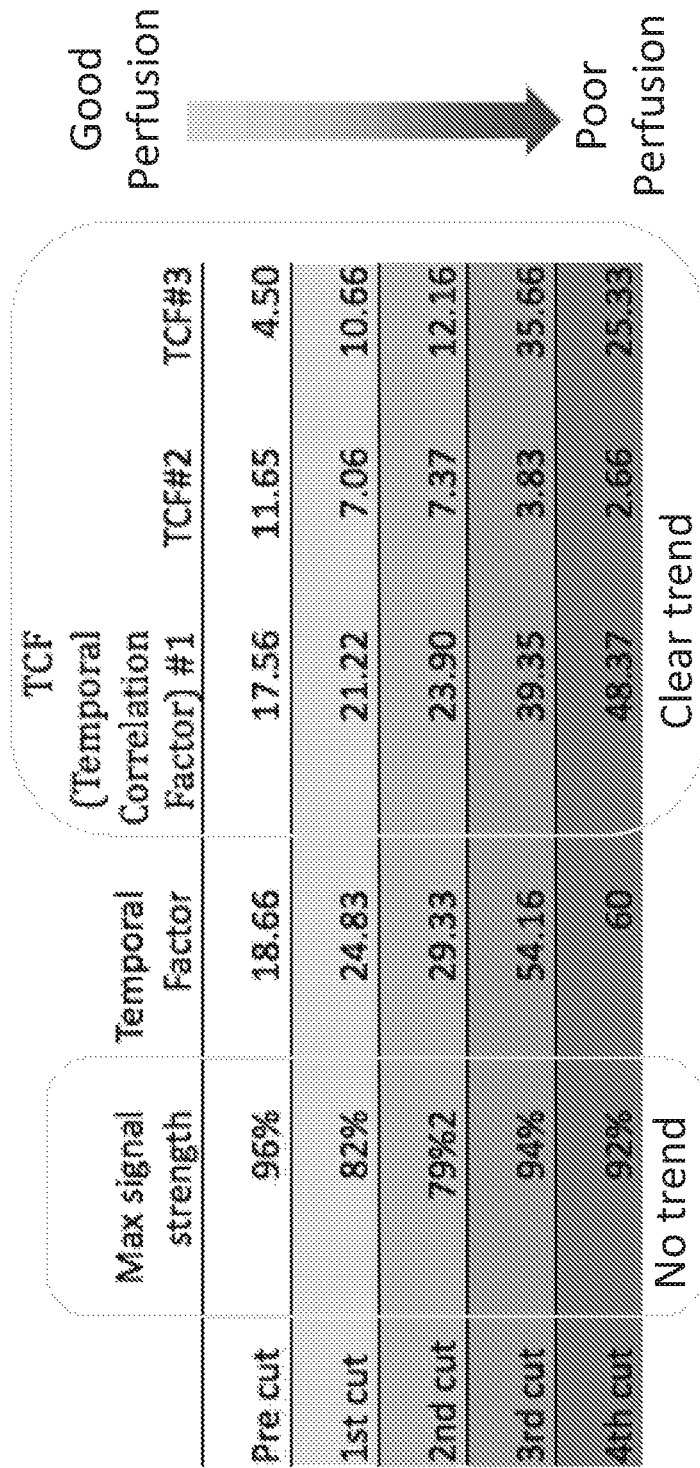

FIG. 6 presents software generated readings of temporal correlation factors for cuts 1-4.

Figure 7:
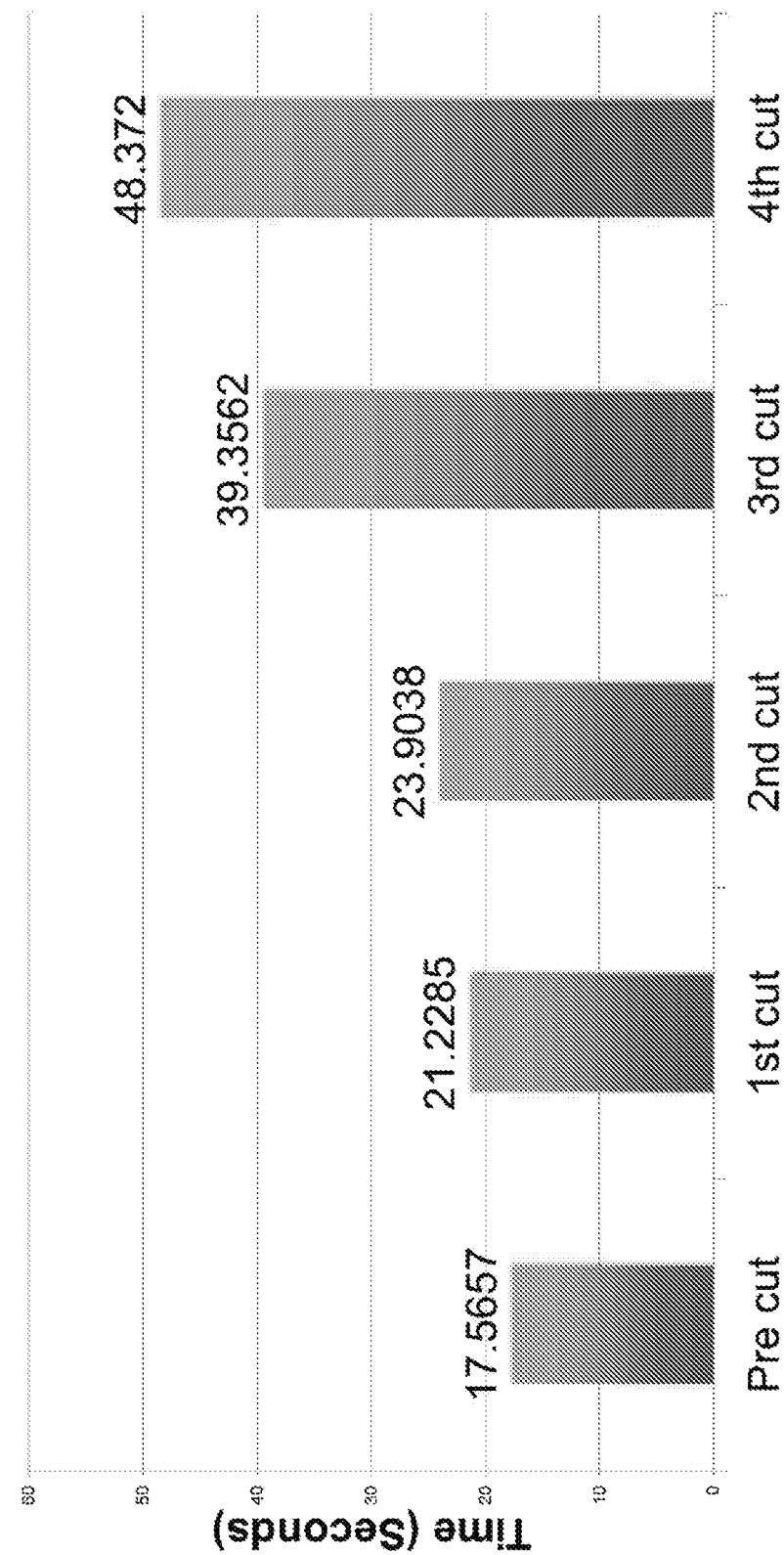

FIG. 7 presents data for temporal correlation factor #1 for each of cuts 1-4.

Figure 8:
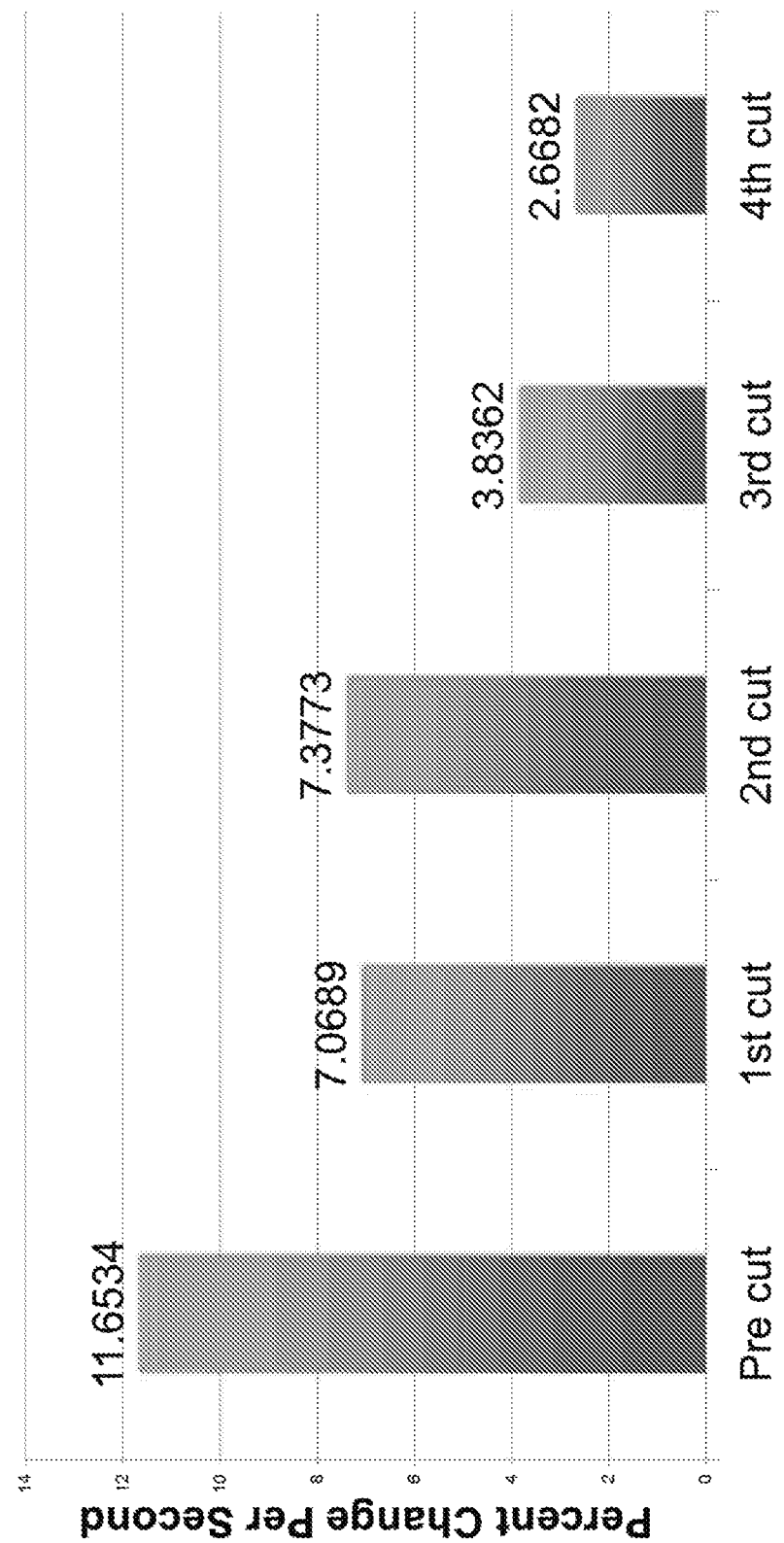

FIG. 8 presents data for temporal correlation factor #2 for each of cuts 1-4.

Figure 9:
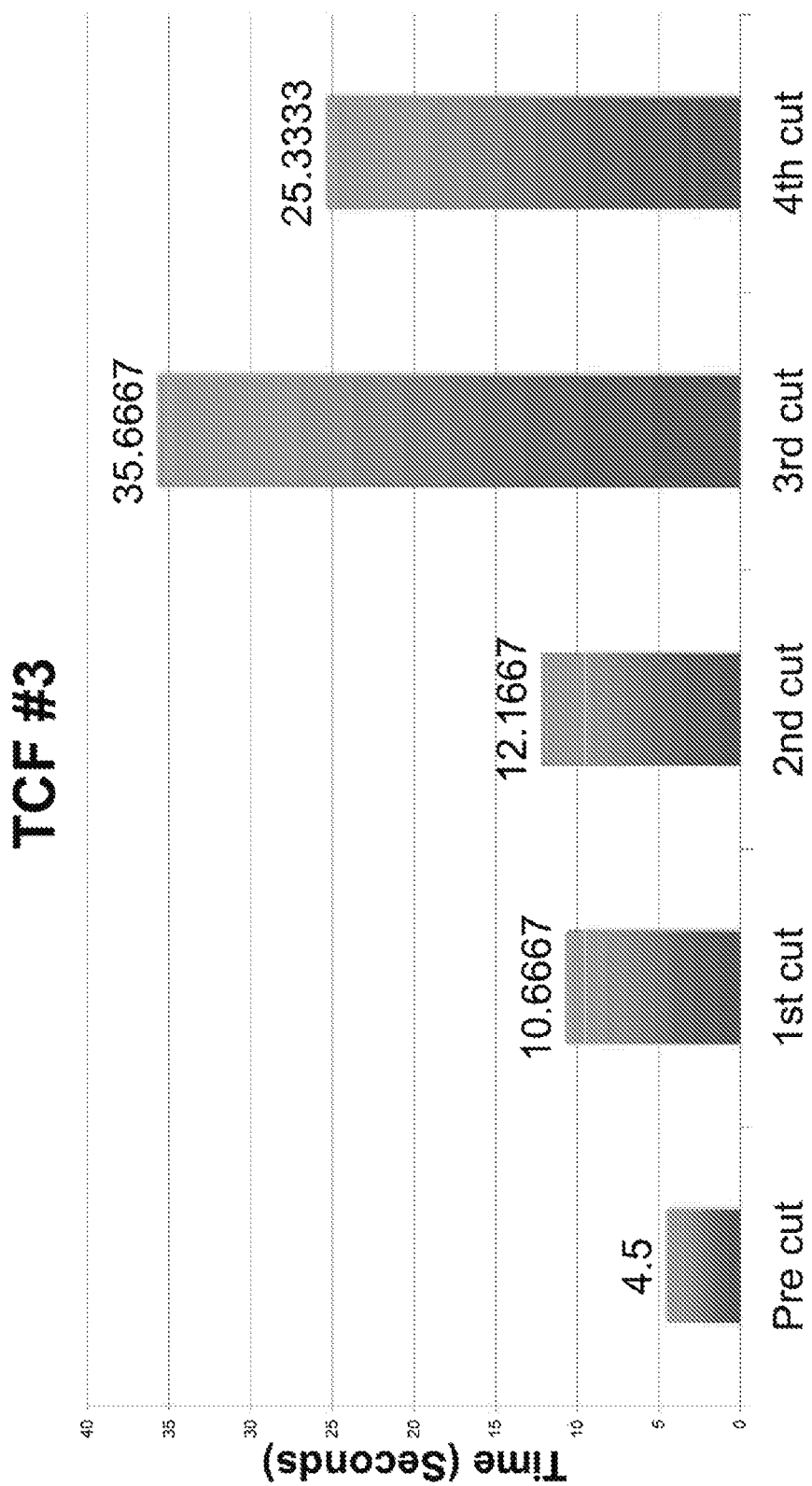

FIG. 9 presents data for temporal correlation factor #3 for each of cuts 1-4.

DETAILED DESCRIPTION

The method for dynamically evaluating blood flow comprises filtering the background noise to obtain dynamic ICG signals, and then performing analysis of ICG intensity as a function of time to make inferences to tissue perfusion and to predict ischemia. Accordingly, a practitioner may objectively determine areas of perfusion in the tissue that is being examined in real-time. In accordance with the principles of the present disclosure, the methods described herein may be used on any digital image file and is therefore not limited by commercial devices.

Referring to FIG. 1, exemplary method 100 for dynamically evaluating blood flow is described. At step 102, the practitioner, e.g., a surgeon, may perform a surgical operation on a patient. At step 104, the practitioner will determine whether it is necessary to know how well a tissue is perfused. If the practitioner determines that it is not necessary to know how well the tissue is perfused, method 100 returns to step 102, and the practitioner continues performing the surgical operation. If the practitioner determines that it is necessary to know how well the tissue is perfused, method 100 proceeds to step 106.

At step 106, ICG is injected into the patient's bloodstream. ICG may be injected using techniques known in the art. At step 108, ICG images, e.g., video, of the target tissue area are recorded and stored. For example, ICG images may be recorded using ICG endoscopic technology known in the art.

At step 110, using a graphical user interface technology known in the art, the practitioner may manually select a region of the video, e.g., range of stored ICG images, that the practitioner would like to analyze. For example, the region of video selected is the range of ICG images from where to collect pixel data regarding the green channel intensity of the ICG images. Data indicative of the selected range of ICG images may be saved, e.g., to a .CSV file, and stored within a memory of a computer.

At step 112, instructions stored within the memory of the computer may cause the data to be automatically normalized and background-filtered in accordance with the principles of the present disclosure. For example, normalizing the data may include generating values, e.g., 3-4, quantifying blood flow in or around the target tissue. In addition, background-filtering the data may include removing noise, and accounting for previous ICG injections into the bloodstream of the patient, e.g., traces of ICG remaining in the tissue that has not been cleared from the body.

At step 114, the normalized and filtered data is used to generate a dynamic representation of ICG perfusion as a function of time, which provides a temporal intensity ruler for measuring how well the tissue is perfused with blood. For example, the dynamic representation may be a graph plotting ICG intensity over time. Based on the dynamic representation, at step 116, the practitioner may make a clinical decision responsive to how well the tissue is perfused. As such, the practitioner may predict ischemia. Method 100 may return to step 104, such that the practitioner continues operating on the patient based on the clinical decision made based on the dynamic representation, until the practitioner must determine whether it is necessary to know how well the tissue is perfused.

Referring now to FIGS. 2A-2D, various steps of the exemplary method of FIG. 1 are provided. For example, FIG. 2A illustrates step 106 of method 100. As shown in FIG. 2A, ICG may be injected into the patient's bloodstream, such that the ICG molecules travel throughout the patient's body and perfuse into tissue. FIG. 2B illustrates step 108 of method 100, wherein ICG images of the tissue are recorded and stored. As shown in FIG. 2B, in one embodiment, the ICG images may be split into "n" number of frames, such that the n frames are stored and may be easily observed by the practitioner at step 110.

FIG. 2C illustrates step 110 of method 100. For example, the practitioner may select the desired range of ICG images by progressing forward or backward through the recorded video data. The recorded video or the "n" number of frames may be displayed on a graphical user interface such that the practitioner may select the desired range with ease. The selected range is then stored for automatic normalization and background-filtering.

FIG. 2D illustrates step 114 of method 100. Specifically, FIG. 2D shows a graph dynamically representing ICG intensity as a function of time. The graph may be generated by running the data saved in the .CVS file through, e.g., MatLab scripts, which may perform calculations to determine local and global maximums and minimums to pinpoint specific times of interest. The dynamic graph allows the practitioner to determine real-time perfusion of tissue, and to make clinical decisions accordingly.

Referring now to FIG. 3, graph 300 illustrating experimental results of a study using methods in accordance with the principles of the present disclosure is described. Specifically, for this study, a computer algorithm was developed and used for filtering and analyzing focal ICG signal as a function of time. As shown in FIG. 3, the algorithm was validated in pig models by serially ligating blood supply from the stomach in 20-minute intervals followed by ICG angiography. This data is compared to pig undergoing sham surgery with the same ICG intervals. Imaging data was collected on the greater curve of the 15 cm below the GE junction. Ligation patterns are: the gastroepiploic arteries ($1^{st}$ Ligation), short gastric arteries ($2^{nd}$ ligation), left gastric artery ($3^{rd}$ ligation), and right gastric artery via distal gastrectomy ($4^{th}$ ligation). The ICG angiography footage from patients undergoing sleeve gastrectomy was retrospectively examined to evaluate the fluorescent signal at the resection staple line. As shown in FIG. 3, the ICG signal intensity of pig stomach after serial blood vessel ligation is illustrated after polynomial fit. The numerical trends are reproducible when compared to the sham surgery pig at each 20 minute mark. Table 1 below depicts the descriptive values of the curves illustrated in FIG. 3.

TABLE 1

|  | Time to Signal Max | Max Rate of Signal Increase | Time to Max Rate of Signal Increase |
| --- | --- | --- | --- |
| No Lig. | 18.67 sec | 11.6 | 3.4 sec |
| $1^{st}$ Lig. | 24.73 sec | 7.1 | 7.1 sec |
| $2^{nd}$ Lig. | 29.33 sec | 7.4 | 6.7 sec |
| $3^{rd}$ Lig. | 54.16 sec | 3.8 | 20.8 sec |
| $4^{th}$ Lig. | 60.00 sec | 2.7 | 43.2 sec |

In human modeling, "before" and "after" ICG footage of a patient undergoing sleeve gastrectomy was evaluated using the same software. The tissue near the staple line had a 45% increase in time to maximum (9.5 to 13.8 seconds), a 35% decrease in max rate of signal increase (17.5 to 11.2), and a 22% (5.1 to 6.3) increase in time to max rate of signal increase, similar to findings in the pig experiment.

The present inventors developed a method and instrumentation for analyzing imaging data to evaluate a blood flow in a patient injected with an imaging agent. The present method and instrumentation may be particularly useful for evaluating a blood flow during a surgical operation on a patient when used with existing surgery imaging technology, such as fluorescent imaging technology.

The method may involve recording a series of images of a tissue of a patient after an injection with an imaging agent, which may be a fluorescent imaging agent, such Indocyanine Green (ICG). After the injection, at least a portion of the images may contain a signal from the imaging agent. In case of a fluorescent imaging agent, the images may be fluorescence images and the signal may be a fluorescent signal. The images may be recorded using an appropriate imaging device, which may be, for example, an endoscopic camera, which may be operatively coupled to a computer system.

As used herein, the term "coupled" may refer to being electrically connected and/or communicatively coupled via one or more interface devices, adapters and the like.

In some embodiments, the recorded images may be stored in a memory of the computer system. Preferably, the recorded and stored images are in a pixel format.

The recorded images may be displayed to a user of the computer system on a monitor or display of the computer system. The user, who may be, for example, a medical professional, such as a doctor, may then select an area of the displayed images, which he or she wants to analyze to evaluate a blood flow. As such, the computer system may receive a feedback from the user regarding the selected area in the images, for which the evaluation of a blood flow will be performed. Upon receiving such feedback, a processor of the computer system may execute calculations normalizing and/or filtering the signal for the selected area of the images. Then the normalized and/or filtered signal may be displayed to the user as function of time to evaluate a blood flow in the tissue of the patient. The normalized and/or filtered signal may be used to determining a clinical status of the patient. In particular, a poor perfusion in the tissue of the patient determined based the normalized and/or filtered signal may indicate a perfusion disease or abnormality in the patient, such as ischemia.

When the images are in a pixel format, the signal used for normalizing and filtering may be an average pixel intensity in the selected area corresponding to the imaging agent. For example, when the images is recorded using a multichannel camera, the signal may be a pixel intensity for a channel, which corresponds to the imaging agent, in the selected area. For example, when the imaging agent is ICG, the signal used for normalizing and filtering may be a pixel intensity for a green channel in the selected area.

In some embodiments, normalizing and/or filtering may involve subtracting a background signal, which may be due to a baseline noise and/or a pre-existing level of the imaging agent in the patient, i.e. a level of the imaging agent in the patient prior to the most recent injection of the imaging agent. To subtract the background signal, pixel signal intensities may be obtained for all the images and then lower (or the lowest) value of intensity may be subtracted from all the pixel signal intensities, essentially re-zeroing pixel intensities. Then, in some embodiments, all re-zeroed signal intensities may assigned values from 0 to 100% (with 100% being a re-zeroed pixel intensity at the end of the measurement (recording)) a percentage of the maximum signal strength reached at the end of the measurement.

In some embodiments, normalizing and/or filtering may involve removing an unsteady portion of the signal, which may be, for example, random noise. In some embodiments, an unsteady portion of the signal may be due to a system noise of the imaging device, such as an endoscopic camera, used to record the images. The removal of the unsteady portion of the signal may be performed on re-zeroed signals as discussed above. In some embodiments, removing an unsteady portion may involve removing a certain portion, e.g. x %, of the bottom of the signal and/or a certain portion, e.g. y % of the bottom of a signal. From a practical point of view, this may mean that a calculation of the time when an imaging agent, such as an ICG was injected, starts when a signal reaches 5% (analysis starts). The analysis may end when the signal reaches 100-y % (100% being a re-zeroed pixel intensity at the end of the measurement (recording)). Values of x and y may depend on a particular level of system noise in the imaging system; and on a particular level of noise reduction desired. In certain cases, x and y may be independently be selected from 0.5%, 1%, 1.5%, 2%, 2.5%, 3%, 3.5%, 4%, 4.5%, 5%, 5.5%, 6%, 6.5%, 7.0%, 7.5%, 8%, 8.5%, 9%, 9.5%, 10%, 11%, 12%, 13%, 14%, 15%. In general, higher values for x and y may lead to a stronger noise reduction but with a risk of some signal data loss. The values of x and y may be selected by the user of the computer system.

In some embodiments, removal of an unsteady portion of the signal involved removing top 5% or top 10% and bottom 5% or bottom 10% of the signal data as they may have represented the system noise when fluorescence is at steady state. In other words, only when the signal strength reached at least 5% or at least 10% from the lowest baseline the calculation of the time the ICG injected was started and the analysis stopped at 95% or at 90% of the signal strength.

In some embodiments, normalizing and/or filtering may involve averaging may involve averaging the signal over two or more images. For example, in some embodiments, the signal may be averaged over three subsequent images. Overall, averaging over a greater number of images may lead to a stronger noise reduction but with a risk of some signal data loss. The values of x and y may be selected by the user of the computer system. The user of the computer system may select a number of images for the averaging.

In some embodiments, the normalized and/or filtered signal may be displayed to the user as an intensity as a function of time. The displayed intensity may be an intensity after the re-zeroing, removing an unsteady portion of the signal and/or averaging the signal over two or more images.

In some embodiments, the normalized and/or filtered signal may be displayed to the user as a temporal correlation factor as a function of time.

In some embodiments, the temporal correlation factor may be a time for the signal in the selected area to reach a stable value from an initial value. In some embodiments, the stable value may be a 100-y % as discussed above and the initial value may be x % value as discussed above. For the ICG data presented in the examples, the initial value was 5% and the stable value was 95% of the maximum signal strength (after re-zeroing). This temporal correlation factor may be related to the cardiac output of the patient as well as microvascular perfusion state of the patient. As such, in some embodiments, this temporal correlation factor when displayed to the user may be used for determining a microvascular perfusion state in the patient with a higher value of this temporal correlation factor indication a poor perfusion in the tissue of the patient and a lower value of this temporal correlation factor indicating a good perfusion in the tissue of the patient.

In some embodiments, normalizing and/filtering the signal may involve calculating a derivative of the signal intensity as a function of time. A derivative of the signal intensity may be calculated in the processor of the computer system using numerical methods known in the art. For example, one may use calculate derivatives using MATLAB. The signal intensity used for the derivative calculations may be an intensity after the re-zeroing, removing an unsteady portion of the signal and/or averaging the signal over two or more images. In some embodiments, the calculated derivative may be a first derivative of the intensity as a function of time.

In some embodiments, the temporal correlation factor displayed to the user may be a derivative of the signal in the selected area as a function of time. In certain embodiments, the derivative may be a first derivative of the signal as a function of time in the selected area. The first derivative as a function of time as a temporal correlation factor may be used for determining a microvascular perfusion state in the tissue of the patient with a lower value of such temporal factor indicating a poor perfusion in the tissue of the patient and a higher value of this temporal correlation factor indicating a good perfusion in the patient.

In some embodiments, the temporal correlation factor displayed to the user may be a time to a maximum of a first derivative of the signal in the selected area. In some embodiments, this temporal correlation factor may be used for determining a for determining a microvascular perfusion state in the tissue of the patient with a higher value of such temporal factor indicating a poor perfusion in the tissue of the patient and a lower value of this temporal correlation factor indicating a good perfusion in the patient.

The present disclosure also provides a system, which may include an imaging device, such as a camera, which may be an endoscopic camera. The imaging device may be configured to record images of a tissue of a patient being inject with an imaging agent, which may be a fluorescent agent, such as ICG. At least some of the recorded images may contain a signal from the imaging agent, e.g. a fluorescent signal from a fluorescent agent, such as ICG. The system may also comprise a memory, which may be coupled to the imaging device, such as a camera, and which may be configured to store the images recorded by the imaging device. The term "memory" may refer to a data storage device or dynamic random access memory (DRAM). The system may also include a display or monitor configured to display information to a user of the system, which may be a medical professional, such as a doctor. For example, the display or monitor may be configured to display to the user the images stored in the memory. The system may also include a user interface, which may be configured to receive a feedback from the user regarding a selected area in the displayed images of the tissue of the patient. The user interface may include, for example, a keyboard, a mouse and/or a touch screen. The system may also include a processing device, which may be operatively coupled to the memory, the interface and the display. The processing device may be configured to execute calculations normalizing and/or filtering the signal from the imaging agent from the selected area of the images. The processing device may send a command to the display or monitor to display the normalized and/or filtered signal to the user. The processing device, the user interface, the display or monitor and the memory may be components of a computing device. The computing device may be provided by a personal computer (PC), a tablet PC, a set-top box (STB), a Personal Digital Assistant (PDA), a cellular telephone, or any computing device capable of executing a set of instructions (sequential or otherwise) that specify operations to be performed by that computing device. The components of the computing device may communicate with each other via a bus.

The present disclosure also provides a non-transitory computer readable storage medium comprising instructions that, when executed by a processor, cause the processor to perform operations comprising: receiving a feedback from a user regarding a selected area in images of a tissue of a patient being injected with an imaging agent, said images comprise signal from the imaging agent; and executing calculations normalizing and/or filtering the signal from the imaging agent for the selected area of the images. The computer readable storage medium may also include instructions that cause the processor to send a command to a display or monitor to display the normalized and/or filtered signal to a user.

Embodiments described herein are further illustrated by, though in no way limited to, the following working examples.

EXAMPLE

Background

Indocyanine Green (ICG) fluorescence imaging has gained popularity for intraoperative evaluation of tissue perfusion. However the current technique lacks reliable quantitative measurements of signal intensity to relate to tissue perfusion. One reason is that the measured ICG signal strength varies from the distance of the camera to tissue, subjecting to user variation. Another is that multiple injections of ICG in the same case results in residual dye from one injection confounding the readings of a later evaluation. As a result, surgeons are often unable to decipher the clinical significance of intra-operative fluorescent images. In this study, we investigate the possibility of using time based intensity change to obtain quantitative data to predict ischemia.

Technology

For this study, a novel computer algorithm was developed for filtering and analyzing focal ICG signal as a function of time. This can be in real time and reduces variability in camera distance and user motion. The steps of the algorithm flow are: 1) Image Capturing from existing fluorescent surgery imaging technology; 2) Film segment selection for imaging analysis; 3) User selection of relevant area and filtering to normalize data 4) Software filtering of flow characteristics relating to intensity and time.

Normalizing and Filtering

The green channel in the RGB signal captured was used for the analysis because the experimental data from the equipment displays the signal as green, but the analysis may be applied to a number of different dye or color capturing technique (including just simple grayscale and white light). The average pixel intensity in the area of interest selected by the user is measured at each time point. Because there is baseline signal in the green channel either due to true baseline noise or pre-existing injection of ICG, it needs to be filtered for the analysis.

To do this, all the data first was captured first. Then, using average green channel signal strength (which is generalizable to any channel dedicated to capturing the signal), the range of signal change was calculated. Lower end of the range is used to subtract from all signal measurements thus essentially re-zeroing the signals. Then, the total signal range is divided up evenly from 0 to 100%. This is then used to reassign the actual value of signal at each time point to a percentage of the maximum signal strength reached at the end of the measurement.

Then the effects of random noise were reduced. The random noise complicates the calculation in order to figure out when the ICG was injected and when it was considered to be its max. In particular, the top 5% and bottom 5% of signal data were removed from analysis as they may represent the system noise when fluorescence is at steady state. Thus, the calculation starts only when signal strength reached at least 5% from lowest baseline as the time the ICG was injected and analysis stops at 95% of signal strength. The user may adjust this range in the software to be even more narrow to reduce effect of noise at steady state but at risk of some data loss.

An additional filter of averaging each data point was performed with the value immediate before and after it, again to reduce noise and artifacts throughout the data capturing process. The user may be allowed to increase the range of this average to include, for example, two or three or more data to be averaged per time point but once again knowing the risk of data loss.

This may give an intensity vs time plot. From this, discrete mathematics may be used to calculate the derivative plot which gives the rate of change of average pixel signal intensity. and from these is how the temporal correlation factors are calculated.

Validation Methods

Pig stomach model is used for validation. Serial ligation of the blood supply to the pig stomach is performed to simulate states of ischemia. ICG angiography is performed before ligation and after each ligation. Imaging analysis was performed at the greater curve of the stomach 15 cm below the GE junction. Ligation occurred at 20 minutes intervals to allow for ICG washout from previous injection. Order of ligation is: the gastroepiploic arteries (1st, Ligation), short gastric arteries (2nd ligation), left gastric artery (3rd ligation), and right gastric artery via distal gastrectomy (4th ligation). FIG. 4 illustrates locations of the cuts for the pig model. Exemplary fluorescent images for cuts 1-4 in the pig model are shown in FIG. 5.

Then ICG anglography footage from patients undergone sleeve gastrectomy to evaluate the fluorescent signal at the resection staple line were retrospectively examined.

Results

The ICG signal intensity of pig stomach after serial blood vessel ligation are recorded and are representative images are seen below. Note the strong visual presence of ICG even after all major blood supply to the stomach has been cut (Cut 4). This is likely due to variable camera distance as well as retained ICG from prior injection.

After processing with the software, the normalized signal strength is related to time below as shown in FIG. 3.

Descriptive values of the curve are in the following table. Max signal strength was not reflective of perfusion before applying the algorithm, but a clear trend could be seen in many variables afterwards, see also FIG. 6.

|  | Pre Algorithm | | Post Algorithm | |
| --- | --- | --- | --- | --- |
|  | % of Max ICG Signal Strength | Adjusted Time to Max Signal Strength | Max Rate of Change (ROC) of Signal | Time of max ROC of Signal |
| Pre cut | 96.72 | 17.56 sec | 11.65 | 4.50 sec |
| $1^{st}$ cut | 82.44 | 21.22 sec | 7.06 | 10.66 sec |
| $2^{nd}$ cut | 78.89 | 23.90 sec | 7.37 | 12.16 sec |
| $3^{rd}$ cut | 93.86 | 39.35 sec | 3.83 | 35.66 sec |
| $4^{th}$ cut | 92.01 | 48.37 sec | 2.66 | 25.33 sec |

Adjusted Time to Max Signal Strength corresponds to Temporal Correlation Factor #1 in FIGS. 6 and 7. Max Rate of Change (ROC) of Signal corresponds to Temporal Correlation Factor #2 in FIGS. 6 and 8. Time of max ROC of Signal corresponds to Temporal Correlation Factor #3 in FIGS. 6 and 9.

Temporal correlation factor #1 was the time to stabilization defined as 90% maximum amplitude of signal strength from initial detection of fluorescence signal (defined >10% of baseline intensity). This may describe the overall rate to maximum intensity time and is related to the cardiac output as well as microvascular perfusion state of the patient Temporal correlation factor #2 was the maximum rate of change of the signal intensity (derivative plot of the intensity graph). This may be a better evaluation of the microvascular status of the tissue that is less dependent on cardiac output of the patient which may be different at baseline as well as their stressed state during surgery. This may be similar to how flow velocity is measured in vascular ultrasound but using visual signal strength instead of doppler signal strength.

Temporal correlation #3 was the time to maximum rate of change of the signal intensity (time to peak on derivative plot mentioned prior). The time it take to reach maximum rate of blood perfusion. This may be an even better surrogate marker of the microvasculature without being affected by background signal intensity or cardiac output.

In human modeling, we evaluated the before and after ICG footage of a patient undergoing sleeve gastrectomy using the software. The tissue near the staple line had a 45% increase in time to maximum (9.5 to 13.8 seconds), a 35% decrease in max rate of signal increase (17.5 to 11.2), and a 22% (5.1 to 6.3) increase in time to max rate of signal increase. These are the same trends we observed in the pig stomach for mild ischemia.

Conclusion

A novel method for quantifying perfusion using ICG by analyzing both signal intensity and time. This algorithm can be used on any digital image file and is therefore not limited by commercial devices.

Additional Embodiments

1. A method for dynamically evaluating blood flow, the method comprising:
2. injecting Indocyanine Green (ICG) into the bloodstream of a patient, such that the ICG perfuses into a tissue of the patient;
3. recording and storing ICG images of the tissue;
4. selecting a range of stored ICG images;
5. automatically normalizing and background-filtering data indicative of the selected range of stored ICG images; and
6. generating a dynamic representation of the ICG perfusion as a function of time based on the normalized and filtered data.
7. The method of embodiment 1, wherein selecting a range of stored ICG images comprises collecting pixel data regarding the green channel intensity of the stored ICG images.
8. The method of embodiment 1, wherein normalizing the data comprises generating values quantifying blood flow in or around the tissue.
9. The method of embodiment 1, wherein background filtering the data comprises accounting for previous ICG injections into the bloodstream of the patient.
10. The method of embodiment 1, wherein the dynamic representation of the ICG perfusion as a function of time is indicative of real-time tissue perfusion.
11. The method of embodiment 1, further comprising:
12. splitting the recorded ICG images of the tissue into n number of frames; and storing the n number of frames of the recorded ICG images, wherein the range of stored ICG images is selected from the n number of frames.
13. The method of embodiment 1, further comprising making a clinical decision based on the dynamic representation of the ICG perfusion as a function of time.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed:

1. A method for dynamically evaluating a blood flow, the method comprising:
    recording images of a tissue of a patient, wherein the images comprise a signal from an imaging agent with which the patient has been injected;
    storing the recorded images in a memory of a computer system;
    displaying the stored images to a user of the computer system;
    receiving a feedback from the user regarding a selected area in the displayed images;
    executing in a processor of the computer system calculations normalizing and/or filtering the signal from the imaging agent for the selected area of the images; and
    displaying the normalized and/or filtered signal as a function of time as a temporal correlation factor as a function of time to evaluate a blood flow in the tissue of the patient, wherein the imaging agent is indocyanine green (ICG) and the images comprise an ICG signal, wherein the ICG signal is pixel data for a green channel intensity in the selected area of the stored images and wherein said executing the calculations comprises digitally subtracting an unsteady portion of the ICG signal, and wherein the temporal correlation factor is a time to maximum of a first derivative of the normalized and/or filtered ICG signal in the selected area.

2. The method of claim 1, wherein said digitally subtracting comprises digitally subtracting at least 5 bottom % of the ICG signal.

3. The method of claim 2, wherein said digitally subtracting comprises digitally subtracting at least 5 top % of the ICG signal.

4. The method of claim 1, further comprising determining a microvascular perfusion state of the patient based on the evaluated value of the temporal correlation factor, wherein a higher value of the temporal correlation factor indicates a poor perfusion in the tissue of the patient.

5. The method of claim 1, wherein the recording is performed by an endoscopic camera.

6. The method of claim 1, wherein said executing the calculations comprises averaging the ICG signal over at least three images.

* * * * *